(12) United States Patent
Bonrath et al.

(10) Patent No.: US 9,248,431 B2
(45) Date of Patent: Feb. 2, 2016

(54) STEPWISE HYDROGENATION OF SPECIFIC ISOPRENOIDS

(71) Applicant: DSM IP ASSETS B.V., Heerlen (NL)

(72) Inventors: Werner Bonrath, Basel (CH); Lioubov Kiwi Minsker, Basel (CH); Igor Iouranov, Basel (CH); Fenrando Cardenas Lizana, Basel (CH); Anne Laure Dessimoz, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/430,239

(22) PCT Filed: Oct. 11, 2013

(86) PCT No.: PCT/EP2013/071238
§ 371 (c)(1),
(2) Date: Mar. 23, 2015

(87) PCT Pub. No.: WO2014/057075
PCT Pub. Date: Apr. 17, 2014

(65) Prior Publication Data
US 2015/0238936 A1    Aug. 27, 2015

(30) Foreign Application Priority Data

Oct. 11, 2012  (EP) ..................................... 12188133

(51) Int. Cl.
| | | |
|---|---|---|
| *C07C 45/62* | (2006.01) |
| *B01J 23/58* | (2006.01) |
| *B01J 37/02* | (2006.01) |
| *B01J 23/44* | (2006.01) |
| *B01J 35/00* | (2006.01) |
| *B82Y 30/00* | (2011.01) |
| *B01J 35/06* | (2006.01) |

(52) U.S. Cl.
CPC ........ *B01J 23/58* (2013.01); *B01J 23/44* (2013.01); *B01J 35/0013* (2013.01); *B01J 35/06* (2013.01); *B01J 37/0211* (2013.01); *B01J 37/0225* (2013.01); *B01J 37/0242* (2013.01); *B01J 37/0244* (2013.01); *B82Y 30/00* (2013.01); *C07C 45/62* (2013.01)

(58) Field of Classification Search
USPC .................................. 568/383, 396, 417, 494
See application file for complete search history.

(56) References Cited

U.S. PATENT DOCUMENTS

| | | | |
|---|---|---|---|
| 2004/0115104 A1 | 6/2004 | Iizuka et al. | |
| 2012/0302801 A1* | 11/2012 | Bonrath | ................... B01J 23/60 568/902 |

OTHER PUBLICATIONS

International Search Report for PCT/EP2013/071238, mailed Jan. 20, 2014, 3 pages.
J. Szykula et al., "Insect Growth Regulators, XVIII. The Synthesis of Doxyl Nitroxides Juvenoids", Liebigs Annalen Der Chemie, vol. 1987, No. 8, Aug. 12, 1987, pp. 709-710.
Mirzoeva et al., "Catalytic Hydrogenation Properties of Pd-and Rh-containing Polymers Immobilized on $Al_2O_3$", Reactive Polymers, vol. 24, No. 3, Feb. 1, 1995, pp. 243-250.

* cited by examiner

*Primary Examiner* — Sudhakar Katakam
*Assistant Examiner* — Pancham Bakshi
(74) *Attorney, Agent, or Firm* — Nixon & Vanderhye P.C.

(57) ABSTRACT

The present invention relates to a stepwise hydrogenation of specific isoprenoids of formula using a specific catalyst.

17 Claims, 2 Drawing Sheets

Figure 1:
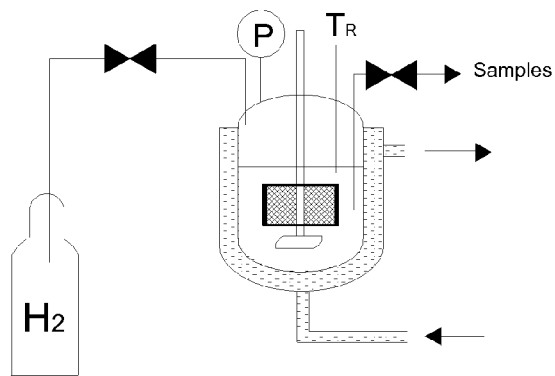
Figure 1:
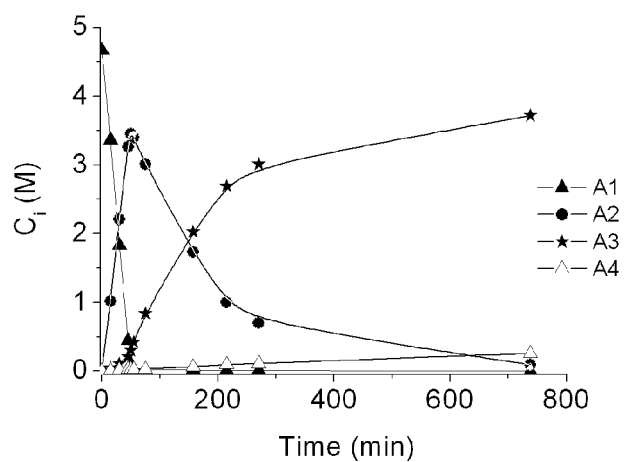

Figure 1. Reactor used for stepwise hydrogenation

Figure 2. Concentration-time profiles over the (0.2%Pd/5%(Al$_2$O$_3$+MgO)/SMFss catalyst (P$_{H2}$=19 bar, T=80°C, n$_{Pl}$/n$_{Pd}$=7500, solvent-free)

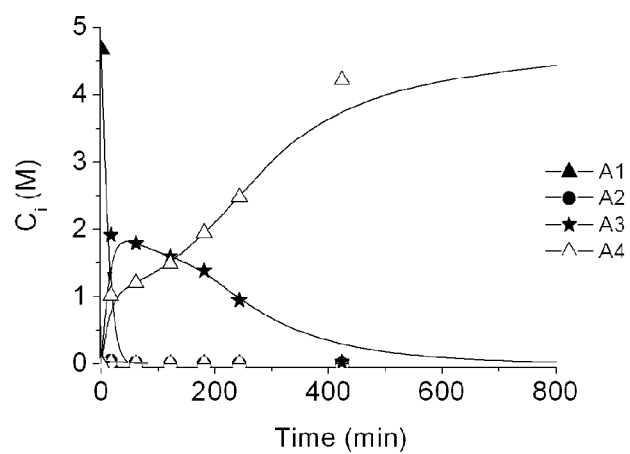
Figure 3. Concentration-time profiles over the 10%Pd/C catalyst ($P_{H2}$=19 bar, T=80°C, $n_{Pl}/n_{Pd}$= 3000, solvent-free)

STEPWISE HYDROGENATION OF SPECIFIC ISOPRENOIDS

This application is the U.S. national phase of International Application No. PCT/EP2013/071238, filed 11 Oct. 2013, which designated the U.S. and claims priority to EP Patent Application No. 12188133.8, filed 11 Oct. 2012, the entire contents of each of which are hereby incorporated by reference.

The present invention relates to a stepwise hydrogenation of specific isoprenoids of formula (I)

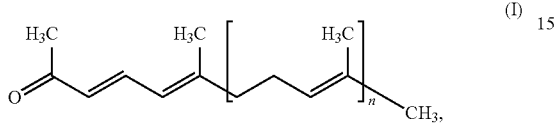

wherein n has a value of 0, 1, 2, 3, 4 or 5.

Isoprenoids are well known compounds. For example pseudoionone (n=1) is compound which can be found and extracted i.e. from tabac plants.

But usually the compounds of formula (I) are produced synthetically.

Pseudoionone, for example, is can be produced out of ethyl acetoacetate as well as out of dehydrolinalool by heating up to 160° C.

Due to fact that the isoprenoids of formula (I) have more than one C—C double bond as well as a C=O bond, there are many possible position where a hydrogenation can take place.

The goal of the present invention was to find a way to hydrogenate compounds of formula (I) selectively and stepwise in the following way:

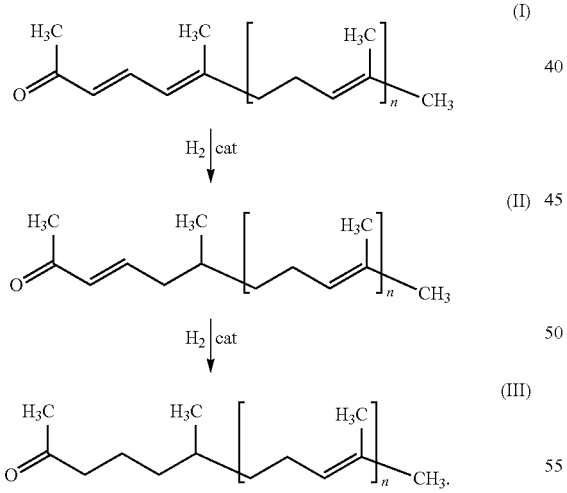

Surprisingly it was found that when a specific catalyst is used, the hydrogenation is taking place stepwise.

Stepwise in the context of the present invention means that the compound of formula (I) is hydrogenated to form the compound of formula (II) before compound of formula (II) is hydrogenated to form compound of formula (III).

The compounds of formula (I) and of formula (II) can have geometrically isomeric arrangement. They can be in the all-E-form, or in the all-Z-form as well as in E/Z-forms. The geometric isomerism is not crucial for the stepwise hydrogenation. Compounds of formula (II) and compounds of formula (III) are useful intermediates in organic synthesis as well as useful compounds in the production of fragrances. Furthermore due to the use of the catalyst of the present invention the following side products:

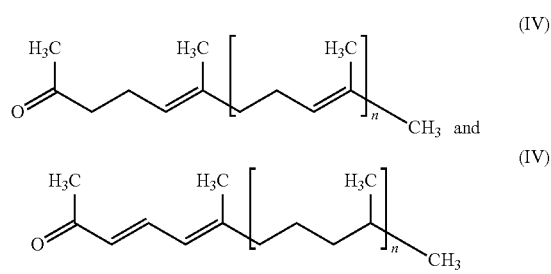

are not obtained (or obtained only in traces).

The catalyst used is a structured catalyst, said catalyst is coated by a non-acidic metal oxide which comprises MgO and optionally at least one further metal oxide, and wherein said non-acidic metal oxide is impregnated with Pd-nanoparticles.

Therefore the present invention relates to a stepwise heterogeneous catalytic hydrogenation of a compound of formula (I)

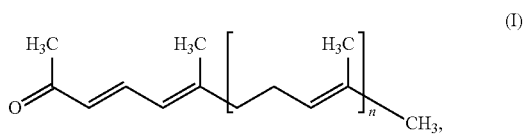

wherein n is 0, 1, 2, 3, 4 or 5,
to, in first step, a compound of formula (II)

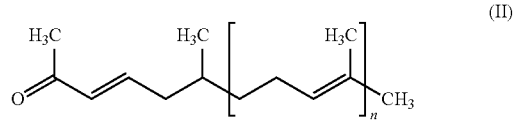

wherein n has the same meaning as in formula (I),
and to, in a second step, a compound of formula (III)

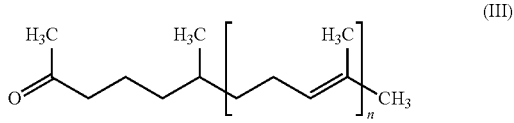

wherein n has the same meaning as in formula (I),
characterised in that
 (i) $H_2$-gas is used to hydrogenate and
 (ii) the catalyst is a structured catalyst coated by non-acidic metal oxide layer, which comprises MgO and optionally at least one further metal oxide, said non-acidic metal oxide layer is impregnated with Pd-nanoparticles.

Preferably the non-acidic metal oxide layer is basic or amphoteric.

The term "structured catalyst" as used herein refers to catalysts wherein the spatial morphology of the catalyst is controlled. Structured catalysts are known in the art, see, e.g., Chimia 56(4), 2002, 159-163. Examples of structured catalysts are ceramic carrier constructions and fibrous structures, especially filamentous woven and non-woven cloths. All types of filamentous woven cloths can be used for use in the present invention. The fibers may be from organic or inorganic matter. Examples are fabrics or fleeces from activated carbon fibers, glass fibers, ceramic fibers, metal fibers composite fibers. The individual fibers of the filamentous woven cloth preferably have a diameter of about 2 μm to about 100 μm, especially a diameter of no more than about 20 μm. The fabrics are suitably woven from threads consisting of a boundle of individual fibers, providing a porous size of the woven cloth of less than about 1 mm. They may be chemically treated, e.g., with nitric acid to modify the specific surface and may have a coating, e.g. of compounds of metals such as Al, Ti or Pb to improve catalytic properties.

Sintered metal fibers (SMF) are also suitable as structured catalyst.

Three-dimensional sintered metal fibers consisting of metallic microfibers have high thermal conductivity that is a great advantage in exothermic hydrogenations, high porosity and permeability. The metal fiber matrix also acts as a micronscale static mixer eliminating channeling. In addition, high mechanical strength, chemical and thermal stability, easy shaping make SMF promising materials for intensification of catalytic hydrogenation.

Suitable SMFs are made from for example FeCrAl alloys as well as from stainless steel.

A more preferred embodiment of the present invention relates to a stepwise hydrogenation of a compound of formula (Ia),

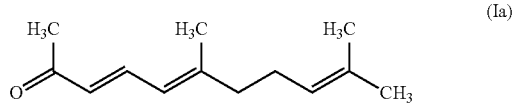

to, in first step, a compound of formula (IIa)

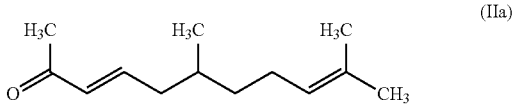

and to, in a second step, a compound of formula (IIIa)

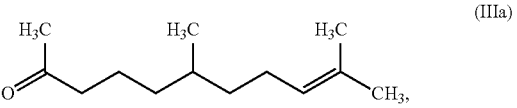

characterised in that
  (i) $H_2$-gas is used to hydrogenate and
  (ii) the catalyst is a structured catalyst coated by a non-acidic oxide layer, which comprises MgO and optionally at least one further metal oxide, said oxide layer is impregnated with Pd-nanoparticles.

A further important advantage of the present invention is that the hydrogenation does not lead to a fully hydrogenated compound (Compound of formula (IV))

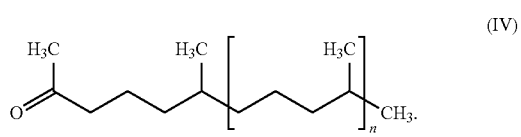

Also the carbonyl group is not reduced as a result of the process according to the present invention.

More preferred processes are characterised in that the catalyst is a structured catalyst based on sintered metal fibers (SMF) coated by a non-acidic oxide layer, which comprises MgO and optionally at least one further metal oxide chosen from the groups consisting of $Al_2O_3$, $TiO_2$, $ZrO_2$, $CeO_2$, $La_2O_3$ (also other oxides made from lanthanide series are suitable), and $Ga_2O_3$, said metal oxide layer is impregnated with Pd-nanoparticles.

Three-dimensional sintered metal fibers (SMF) consisting of metallic microfibers are the preferred as structured catalyst support. SMF have high thermal conductivity, which is a great advantage in exothermic hydrogenations, as well as high porosity and high permeability.

Suitable sintered metal fibers in the context of the present invention are as mentioned before i.e. FeCrAl alloys or stainless steel.

Such materials are commercially available for example from Bekaert SA (Belgium).

The non-acidic oxide layer is substantially free from any Zn. This means that the non-acidic oxide layer is free from Zn in any form (Zn in elemental form as well as Zn in any other form).

In a preferred embodiment of the present invention the SMF is made from a FeCrAl alloy, which optionally can be preoxidised.

In a preferred embodiment of the present invention the SMF is made from stainless steel alloy.

The SMF is coated by a thin layer of at least one non-acidic metal oxide. Preferably the metal oxide is MgO and optionally at least one further metal oxide. These other metal oxides are chosen from the group consisting of $Al_2O_3$, $TiO_2$, $ZrO_2$, $CeO_2$, $La_2O_3$ and $Ga_2O_3$.

More preferred the SMF is coated by a mixture consisting of MgO and $Al_2O_3$.

Usually the catalyst comprises from 0.01 weight-% (wt-%) up to 20 wt-%, based on the total weight of the catalyst, of the non-acidic metal oxide layer.

Preferably 0.1-10 wt-%, more preferably 1.5-10 wt-%, most preferably 2-8 wt-%, based on the total weight of the catalyst.

The non-acidic metal oxide layer is impregnated with Pd-nanoparticles.

Usually the Pd-nanoparticles have a size between 0.5 and 20 nm, preferably between 2 and 15 nm, more preferably between 2 and 12 nm and most preferably between 3 to 9 nm.

The present invention further relates to a process as defined above, wherein the catalyst is containing between 0.001 and 5 wt-% of Pd-nanoparticles, preferably between 0.01 and 2 wt-% more preferably between 0.05 and 1 wt-% and most preferably between 0.2 and 0.8 wt-%, based on the total weight of the catalyst.

The hydrogenation is carried out at elevated temperatures. Usually the hydrogenation is carried out at a temperature of 40-120° C.

The hydrogenation is carried out at a pressure of 1-200 bar.

The hydrogenation can be carried out in solvent (or a mixture of solvents) or it can be carried out without any solvent.

When using a solvent, an inert solvent (or mixture of inert solvents) must be used.

Preferably, when a solvent is used, at least one alcohol or a mixture of water and at least one alcohol is used.

More preferred are methanol, ethanol, propanol, i-propanol and any mixture of these, as well as in combination with water. (especially an ethanol/water-mixture)

Furthermore the catalyst used in the stepwise hydrogenation is new as well.

Therefore the present invention also relates to a structured catalyst coated by a non-acidic metal oxide layer, which comprises MgO and optionally at least one further metal oxide, said oxide layer is impregnated with Pd-nanoparticles.

All preferences as listed and defined for the process above also apply for the catalyst.

A more preferred catalyst is a structured catalyst based on sintered metal fibers (SMF) coated by a non-acidic oxide layer, which comprises MgO and optionally at least one further metal oxide chosen from the groups consisting of $Al_2O_3$, $TiO_2$, $ZrO_2$, $CeO_2$, $La_2O_3$ and $Ga_2O_3$, said metal oxide layer is impregnated with Pd-nanoparticles.

A preferred embodiment of the present invention relates to a catalyst comprising SMF made from a FeCrAl alloy, which optionally can be preoxidised.

In a preferred embodiment of the present invention the SMF is made from stainless steel alloy.

A preferred embodiment of the present invention relates to a catalyst comprising SMF coated by a thin layer of at least one non-acidic metal oxide. Preferably the metal oxide is MgO and optionally at least one further metal oxide. These other metal oxides are chosen from the group consisting of $Al_2O_3$, $TiO_2$, $ZrO_2$, $CeO_2$, $La_2O_3$ and $Ga_2O_3$.

A more preferred embodiment of the present invention relates to a catalyst comprising SMF coated by a mixture consisting of MgO and $Al_2O_3$.

Therefore the present invention relates to a structured catalyst coated by a non-acidic metal oxide layer, which comprises MgO and $Al_2O_3$, said metal oxide layer is impregnated with Pd-nanoparticles.

The present invention also relates to a catalyst comprising from 0.01 wt-% up to 20 wt-%, based on the total weight of the catalyst, of the non-acidic metal oxide layer.

Preferably 0.1-10 wt-%, more preferably 1.5-10 wt-%, most preferably 2-8 wt-%, based on the total weight of the catalyst.

The non-acidic metal oxide layer of the catalyst according to the present invention is impregnated with Pd-nanoparticles.

Usually the Pd-nanoparticles have a size between 0.5 and 20 nm, preferably between 2 and 15 nm, more preferably between 2 and 12 nm and most preferably between 3 to 9 nm.

Also an important advantage is that the catalyst according to the present invention can be reused and that the selectivity is remaining at a very good level.

The present invention further relates to a catalyst containing between 0.001 and 5 wt-% of Pd nanoparticles, preferably between 0.01 and 2 wt-% more preferably between 0.05 and 1 wt-% and most preferably between 0.2 and 0.8 wt-%, based on the total weight of the catalyst.

Therefore the present invention relates to a structured catalyst as described above, wherein the catalyst comprises from 0.01 wt-% up to 20 wt-%, based on the total weight of the catalyst, of the non-acidic metal oxide layer, and wherein the Pd-nanoparticles have a size between 0.5 and 20 nm, and wherein the catalyst comprises between 0.001 and 5 wt-% of Pd nanoparticles, based on the total weight of the catalyst.

FIGURES

FIG. 1: Reactor used for stepwise hydrogenation

FIG. 2: Concentration-time profiles (0.2% Pd/5%($Al_2O_3$+MgO)/$SMF_{SS}$ catalyst, solvent-free)

FIG. 3: Concentration-time profiles (10% Pd/C catalyst, solvent-free)

The following examples serve to illustrate the invention. If not otherwise stated all parts are given are related to the weight and the temperature is given in ° C.

EXAMPLES

Example 1

Preparation of a Structured Catalyst (0.2% Pd/5% (MgO+$Al_2O_3$)/$SMF_{SS}$)

The AISI316L stainless steel sintered metal fiber panel ($SMF_{SS}$, Bekaert Fibre Technology) were washed in acetone (Fluka, ≥99%), boiled in toluene (Fluka, ≥99.7%) for 30 min and air-dried at room temperature. The filters were further oxidised in air (ramp—20° $min^{-1}$) at 450° C. for 2 h to facilitate the adhesion of the oxide layer to the metal fiber surface.

After the pre-treatment the $SMF_{SS}$ panel was dip-coated by a MgO+$Al_2O_3$ (molar ratio 1:1) layer. A MgO+$Al_2O_3$ precursor solution was prepared as following: 200 g of $Al(NO_3)_3 \cdot 9H_2O$ were dissolved in 700 ml of distilled water. The solution was heated up to 95° C. 22.0 g of MgO were added to the solution. Heating and stirring were maintained until MgO was completely dissolved. The solution was then cooled down to room temperature.

MgO+$Al_2O_3$ (molar ratio 1:1) layer deposition was performed by dipping $SMF_{SS}$ panel into the MgO+$Al_2O_3$ precursor solution followed by drying in air at room temperature (1 h) and calcination at 450° C. (1 h, temperature ramp—2°/min). The dipping-drying-calcination cycle was repeated 2 times to deposit ~5 wt. % of MgO+$Al_2O_3$ (molar ratio 1:1).

The 5%(MgO+$Al_2O_3$)/$SMF_{SS}$ panel was then impregnated by a Pd nanoparticles sol. The Pd nanoparticles sol was prepared as following: 0.277 g of poly(N-vinyl-2-pyrrolidone) (K 30, M~50000) and 0.156 g of ascorbic acid were dissolved in 15 ml of hot (95-98° C.) water (Solution 1). In another beaker, 0.088 g of $PdCl_2$ and 0.058 g of NaCl were dissolved in 10 ml of hot water (Solution 2). Solution 2 was added fast to Solution 1 under stirring. The solution color changed immediately from brown to black indicating Pd nanoparticles formation. The obtained colloid solution was kept under stirring and heating for 3 hours. Then, the sol was cooled down and diluted by 75 ml of acetone. The mixture was left for the night without stirring. The colorless liquid phase was discarded. The black viscous residue was dissolved in 12.5 ml of water giving a stable Pd sol.

The 5%(MgO+$Al_2O_3$)/$SMF_{SS}$ panel was impregnated by a Pd nanoparticles sol followed by drying in air at room temperature (1 h) two times. The 0.2% Pd/5%(MgO+$Al_2O_3$)/$SMF_{SS}$ panel was calcined in air at 600° C. (2 hours) and then reduced in a 10% $H_2$+90% Ar flow (flow rate—450 ml/min) at 300° C. (2 hours).

Example 2 (Comparison Example)

Preparation of the 0.2% Pd/5% ZnO/SMF$_{Fecral}$ Catalyst

A SMF$_{Fecral}$ panel cleaned as described in Example 1 was dip-coated by a Zn oxide layer. A ZnO precursor solution was prepared as following: 18.3 g of monoethanolamine and 12.8 g of acetoin are dissolved in 0.75 l of iso-propanol under stirring. Then, 65.8 g of Zn(CH$_3$COO)$_2$.2H$_2$O were added to the mixture and dissolved under stirring.

ZnO layer deposition was performed by dipping SMF$_{Fecral}$ panel into the ZnO precursor solution followed by drying in air at room temperature (0.5 h) and calcination at 600° C. (0.5 h). The dipping-drying-calcination cycle was repeated 6 times to deposit ~5 wt. % of ZnO. Coated SMF$_{Fecral}$ panel was then post-annealed at 900° C. for 15 min.

Pd was deposited on the 5% ZnO/SMF$_{Fecral}$ panel as described in Example 1.

Example 3 (Comparison Example)

Preparation of the 0.2% Pd/5%(ZnO+Al$_2$O$_3$)/SMF$_{SS}$ Catalyst

The 0.2% Pd/5%(ZnO+Al$_2$O$_3$)/SMF$_{SS}$ catalyst was prepared as described in Example 1 but MgO was replaced by ZnO.

Example 4

Stepwise Hydrogenation Using the Catalysts of Example 1-3 in a Solvent

All hydrogenations in a solvent were carried by using the experimental set-up shown in FIG. 1. The SMF based catalyst (0.8 g, Example 1, 2 or 3) was fixed on the stirrer. 60 cm$^3$ of organic solution (solvent+starting material (~32%) were charged into the reactor. The reactor was purged three times with N$_2$, heated up to the reaction temperature and pressurized with H$_2$. The pressure was kept constant during the reaction. The reaction mixture is stirred (with 2000 rpm). The reaction progress was followed by withdrawing samples (~0.5 cm$^3$) and analysis.

Example 5

Stepwise Hydrogenation Under Solvent-Free Conditions

The hydrogenation was carried out as described in Example 4, but without any solvent. In this case, 60 cm$^3$ of starting material were charged into the reactor.

Example 6

Stepwise Hydrogenation Using 10% Pd/C Catalyst as Catalyst

The hydrogenation was carried out as described in Example 4, but the SMF based structured catalyst was replaced by a commercially available Pd supported on powdered activated carbon 10% Pd/C (~0.04 g, Fluka). In this case, the powdered catalyst was mixed with the liquid phase.

Example 7

Stepwise Hydrogenation of Pseudoionone Using 0.2% Pd/5%(MgO+Al$_2$O$_3$)/SMF$_{SS}$ Catalyst The hydrogenation of pseudoionone (compound of formula (Ia)≡compound A$_1$)

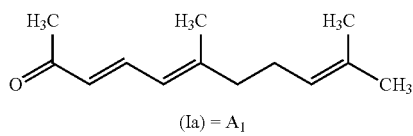

(Ia) = A$_1$ was carried out as described in Example 5 using the catalyst of Example 1. The obtained concentration-time profiles as well as the reaction conditions are shown in FIG. 2.

As seen in FIG. 2, in this case pseudoionone hydrogenation is a stepwise process. The concentration of pseudoionone (compound A$_1$) decreases rapidly and the concentration of compound of formula (IIa) (≡compound A$_2$)

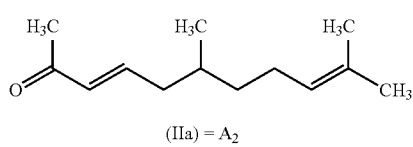

(IIa) = A$_2$ goes through a maximum. After full conversion of A$_1$, compound of formula (IIIa) (≡compound A$_3$)

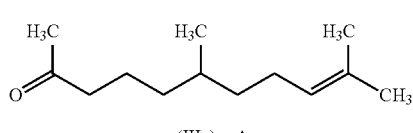

(IIIa) = A$_3$ starts to be produced. The production of A$_4$

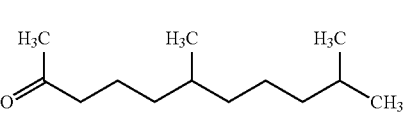

A$_4$ is negligible. No alcohol (A$_5$) formation

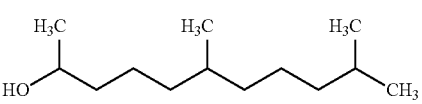

A$_5$ was observed.

Example 8

Pseudoionone Hydrogenation Using a 10% Pd/C Catalyst

The pseudoionone hydrogenation was carried out as described in Example 5 using the 10% Pd/C catalyst (Fluka). The obtained concentration-time profiles as well as the reaction conditions are shown in FIG. 3. In this case, the formation of $A_2$ is not observed; $A_3$ and $A_4$ are formed immediately after the start of the reaction.

Example 9

Stepwise Hydrogenation of Pseudoionone Using the SMF-Based Catalysts of Examples 1-3

The pseudoionone hydrogenation was carried out as described in Example 5 using the catalysts prepared as described in Examples 1-3. The measured initial catalyst activity $R_{PI}$ and selectivity $S_{A2}$ are presented in Table 1.

TABLE 1

Initial activity and $A_2$ selectivity obtained in PI hydrogenation over the SMF-based catalyst ($P_{H2}$ = 19 bar, T = 80° C., $n_{PI}/n_{Pd}$ = 7400, solvent-free)

| CATALYST | $R_{PI}$, mol PI/mol Pd/s | $S_{A2}$, % |
|---|---|---|
| 0.2% Pd/5% ZnO/SMFss | <0.1 | |
| 0.2% Pd/5%($Al_2O_3$ + ZnO)/SMFss | 1.6 | 66 |
| 0.2% Pd/5%($Al_2O_3$ + MgO)/SMFss | 2.5 | 78 |

It can be seen that the catalyst according to the present invention shows improved catalytic properties (selectivity).

Example 10

Stepwise Hydrogenation of Pseudoionone in Different Solvents

The pseudoionone hydrogenation was carried out as described in Example 4 using the catalysts prepared as described in Example 1. The measured initial catalyst activity $R_{PI}$ and selectivity $S_{A2}$ are presented in Table 2.

TABLE 2

Influence of the solvent on the initial activity and $A_2$ selectivity obtained in PI hydrogenation over the 0.2% Pd/5%(MgO + $Al_2O_3$)/ SMFss catalyst ($P_{H2}$ = 19 bar, T = 80° C., $n_{PI}/n_{Pd}$ = 7400)

| SOLVENT | $R_{PI}$, mol PI/mol Pd/s | $S_{A2}$, % |
|---|---|---|
| Toluene | 4.9 | 75 |
| Isopropanol | 6.3 | 81 |
| Ethanol | 5.8 | 83 |
| Ethanol + water (7:1*) | 4.1 | 88 |
| Ethanol + water (3:1*) | 2.9 | 91 |

*wt ratio

It can be seen that the reaction works in solvents. It works especially well in alcohols and alcohol/water mixtures.

Furthermore the re-usability of the 0.2% Pd/5%(MgO+ $Al_2O_3$)/$SMF_{SS}$ catalyst was tested. It was used under the experimental conditions of example 4 and afterwards washed with ethanol and dried at room temperature. Even after 5 cycles the selectivity was more than 90%.

The invention claimed is:

1. A stepwise heterogeneous catalytic hydrogenation process which comprises:
   (1) a first step of hydrogenating a compound of formula (I)

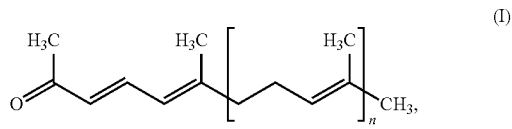

(I)

wherein n=0, 1, 2, 3, 4 or 5,
   to a compound of formula (II)

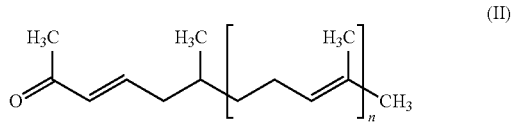

(II)

wherein n has the same meaning as in formula (I), and thereafter
   (2) a second step of hydrogenating the compound of formula (II) to a compound of formula (III)

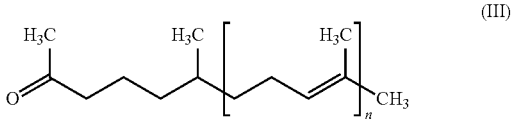

(III)

wherein n has the same meaning as in formula (I), wherein
   (i) $H_2$-gas is used for hydrogenation, and
   (ii) hydrogenation is conducted in the presence of a structured catalyst coated by a non-acidic metal oxide layer impregnated with Pd-nanoparticles, wherein the non-acidic metal oxide layer comprises MgO and optionally at least one further metal oxide, and is substantially free from any Zn.

2. The stepwise heterogeneous catalytic hydrogenation process according to claim 1, wherein the compound of formula (I) is a compound of formula (Ia),

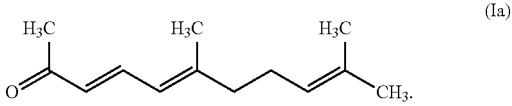

(Ia)

3. The stepwise heterogeneous catalytic hydrogenation process according to claim 1, wherein the structured catalyst is based on sintered metal fibers (SMF).

4. The stepwise heterogeneous catalytic hydrogenation process according to claim 1, wherein SMF is FeCrAl alloys or stainless steel.

5. The stepwise hydrogenation process according to claim 1, wherein the catalyst comprises from 0.01 wt-% up to 20 wt-%, based on the total weight of the catalyst, of the non-acidic metal oxide layer.

6. The stepwise heterogeneous catalytic hydrogenation process according to claim 1, wherein the Pd-nanoparticles have a size between 0.5 and 20 nm.

7. The stepwise heterogeneous catalytic hydrogenation process according to claim 1, wherein the catalyst comprises between 0.001 and 5 wt-% of the Pd-nanoparticles.

8. The stepwise heterogeneous catalytic hydrogenation process according to claim 1, wherein the hydrogenation process is carried out in a solvent.

9. The stepwise heterogeneous catalytic hydrogenation process according to claim 8, wherein the solvent is at least one alcohol optionally in combination with water.

10. The stepwise heterogeneous catalytic hydrogenation process according to claim 1, wherein the hydrogenation process is carried out without any solvents.

11. The stepwise heterogeneous catalytic hydrogenation process according to claim 1, wherein the hydrogenation process is carried out at a temperature of 40-120° C.

12. The stepwise heterogeneous catalytic hydrogenation process according to claim 1, wherein the hydrogenation process is carried under a pressure of 1-200 bar.

13. The stepwise heterogeneous catalytic hydrogenation process according to claim 6, wherein the size of the Pd-nanoparticles is between 2 and 15 nm.

14. The stepwise heterogeneous catalytic hydrogenation process according to claim 6, wherein the size of the Pd-nanoparticles is between 3 and 9 nm.

15. The stepwise heterogeneous catalytic hydrogenation process according to claim 7, wherein the catalyst comprises between 0.01 and 2 wt-% of the Pd-nanoparticles.

16. The stepwise heterogeneous catalytic hydrogenation process according to claim 7, wherein the catalyst comprises between 0.05 and 1 wt-% of the Pd-nanoparticles.

17. The stepwise heterogeneous catalytic hydrogenation process according to claim 7, wherein the catalyst comprises between 0.2 and 0.8 wt-% of the Pd-nanoparticles.

\* \* \* \* \*